United States Patent [19]
Hofer et al.

[11] 3,954,847
[45] May 4, 1976

[54] NEW BENZENE PHOSPHONOUS ACID COMPOUNDS, THEIR PRODUCTION AND USE AS STABILIZERS FOR ORGANIC MATERIALS

[75] Inventors: Kurt Hofer, Muenchenstein; Guenther Tscheulin, Riehen, both of Switzerland

[73] Assignee: Sandoz Ltd., Basel, Switzerland

[22] Filed: Apr. 25, 1974

[21] Appl. No.: 463,866

Related U.S. Application Data

[62] Division of Ser. No. 191,079, Oct. 20, 1971, Pat. No. 3,825,629.

[30] Foreign Application Priority Data
Oct. 22, 1970 Switzerland.................... 15605/70
June 30, 1971 Switzerland.................... 9597/71

[52] U.S. Cl. ................ 260/502.4 P; 252/8.6; 252/300; 260/45.75 P; 260/107; 260/293.51; 260/326.8; 260/45.75 PS
[51] Int. Cl.² ........................................ C07F 9/48
[58] Field of Search ...................... 260/502.4 P

[56] References Cited
UNITED STATES PATENTS
3,493,639  2/1970  Tars................ 260/502.4 P
3,702,878  11/1972  Saito................ 260/502.4 P
3,825,629  7/1974  Hofer et al................ 260/502.4 P

OTHER PUBLICATIONS

Frank, "Chem. Rev.," Vol. 61 (Aug. 1961), pp. 389,393,395,422.

Freedman, "J. Am. Chem. Soc.," Vol. 77 (1955), pp. 6223–6224.

*Primary Examiner*—Joseph E. Evans
*Attorney, Agent, or Firm*—Gerald D. Sharkin; Richard E. Vila; Thomas C. Doyle

[57] ABSTRACT

The purpose of the invention are new benzene phosphorous acid compounds in which two to four benzene nuclei are bound together and which contain one to three phosphorus atoms. The new compounds are free acids, their salts with inorganic cations, their esters, thioesters or amides. The invention concerns also the manufacture of these benzene phosphonous acid compounds and their use for the stabilization of organic materials.

6 Claims, No Drawings

NEW BENZENE PHOSPHONOUS ACID COMPOUNDS, THEIR PRODUCTION AND USE AS STABILIZERS FOR ORGANIC MATERIALS

This application is a division of our copending application Ser. No. 191,079 filed Oct. 20, 1971 and now U.S. Pat. No. 3,825,629.

The purpose of the invention are new benzene phosphonous acid compounds in which two to four benzene nuclei are bound together and which contain one to three phosphorus atoms. The new compounds are free acids, their salts with inorganic cations, their esters, thioesters or amides. The invention concerns also the manufacture of these benzene phosphonous acid compounds and their use for the stabilization of organic materials.

The invention relates to a process for the production of new benzene phosphonous acid compounds of formula

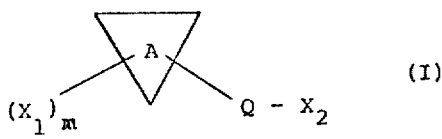

wherein
$m$ means 1 or 2,
A unsubstituted or substituted diphenyl or terphenyl,
Q the single bond or an unsubstituted or substituted phenylene radical,
$X_1$ a radical of formula

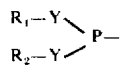

and $X_2$ hydrogen or a radical of formula

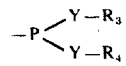

$R_1$, $R_2$, $R_3$ and $R_4$ independent of each other stand for hydrogen or an unsubstituted or a substituted hydrocarbon radical, containing up to 16 carbon atoms,
Y for oxygen, sulfur or the radical of formula

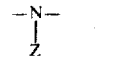

and Z, either bound to R, together with the Z-atom, for a heterocyclic ring or for $R_1$, $R_2$, $R_3$ or $R_4$, which process is characterized by the reaction of 1 mol of a compound of formula

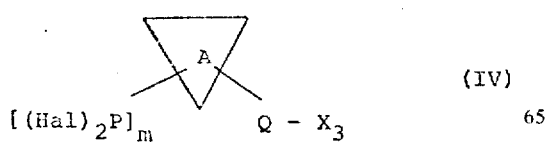

wherein (Hal) means halogen and $X_3$ hydrogen or a radical of formula

with so many mols of a compound of formula

or of a mixture of 2, 3 or 4 compounds of formulae $R_1 — Y — H$, $R_2 — Y — H$, $R_3 — Y — H$ and $R_4 — Y — H$, as Hal-radicals are present in the compound of formula (IV).

The starting materials of formula (IV) used in the present invention are new. They are produced from unsubstituted or substituted aromatic hydrocarbons, which are composed of 2, 3 or 4 benzene nuclei, bound together by a single bond. Examples for such hydrocarbons are: Diphenyl, o-, m- and p- terphenyl, m- quaterphenyl, p- quaterphenyl, 1,2,4-triphenyl-benzene and 1,3,5-triphenyl-benzene. From these starting materials the compounds of formula (IV) are produced by reaction with a phosphorus trihalide, preferably with phosphorus trichloride. This reaction can be performed at very high temperatures in the gaseous phase. To avoid side-reactions it is, generally, advantageous to work under milder conditions, using catalysts. Friedel-Crafts-Catalysts are suitable, especially anhydrous aluminium chloride. One preferably works with a surplus of phosphorus trichloride at its boiling temperature. Working up the reaction mixture, the aluminium chloride complex with the dichlorophosphine is first decomposed, for instance with phosphorus oxychloride or with pyridine. Principally these methods of manufacture are known. These and other analogous procedures for the production of compounds of formula (IV) are collectively described by K. Sasse in "Handbuch von Houben-Weyl, Methoden der organischen Chemie, 4th Edition (1963), Vol. XII/1, organische Phosphorverbindungen", part 1, pages 302–318.

The starting materials, characterized by formula (VI), are: Water, hydrogen sulfide, ammonia, alcohols, phenols, mercaptans, thiophenols and organic primary and secondary amines.

The reaction of the starting materials of formulae (IV) and (VI) normally proceeds easily; to avoid side-reactions, it is often necessary to smooth the vehement reaction by cooling externally. Reacting with water, it is preferred to use it in surplus, to cool and to add the halophosphine of formula (IV) so slowly, that the temperature does not rise too high by the exothermic reaction. Accomplishing the hydrolysis in this way, there result colorless, powdery compounds, containing radicals of the following structure:

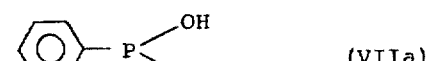

These derivatives of the benzene phosphonous acid have acid properties and, by treating with inorganic bases or with salts containing inorganic cations, are transferred in their corresponding salts. Examples for such inorganic reagents are: Calcium hydroxide, zinc-oxide, sodium carbonate, potassium hydrogen carbonate, aluminium acetate, barium chloride, nickel acetate and zinc chloride.

The present invention is particularly concerned with products of the above type which are of the formula

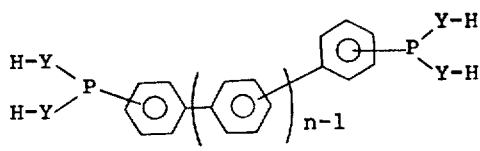

wherein Y is oxygen or sulphur and $n$ is 1 or 2. The hydrolysis of halophosphines of formula (IV) and the transformation of the hydrolysis products, which contain radicals of the above formulae (VIIa) or (VIIb) into their salts, may also be performed in a one step process. For this purpose, as described above, the water used for the hydrolysis is put in surplus in advance, together with the desired inorganic reagent, followed by the halophosphine of formula (IV), which is slowly added by stirring. Humidity is carefully excluded if, instead of water, other compounds of formula (VI) are to be reacted. Generally phenols react smoothly if heated for instance to 100°–150°C, whereby the hydrogen halide splits off.

Acid binding agents, such as pyridine or trialkylamines can be added to bind the split off hydrogen halide.

This method is preferred if alcohols are reacted. If the compounds of formula (IV) are reacted with organic amines or with ammonia, these are used in a surplus, which serves as a binding agent for the hydrogen halide split off.

The described reactions are analogous processes, which are generally known. A respective collective summary has been published in the afore-mentioned book by K. Sasse (compare p.318 ff.).

Substituents in the polyphenyl compounds, characterized by the symbol $\overline{\Psi}$ [formulae (I) and (IV)], in the phenylene radical Q and also as radicals R [formulae (II) and (VI)] and Z [formula (III)] are alkyl- and cycloalkyl groups. Examples for such substituents are: Methyl, ethyl, propyl, butyl, isobutyl, amyl, 2,2-dimethylpropyl, octyl, dodecyl, isopropyl, tert.-butyl, 2,6,8-trimethyl-4-nonyl, 2-ethyl-hexyl, 2,4,6,8-tetramethylnonyl, cyclododecyl.

The preferred polyphenyl compounds and the phenylene radical Q are unsubstituted; they may be substituted by halogen, especially by chlorine and bromine or by alkoxy radicals such as methoxy, ethoxy, propoxy, isopropoxy, butoxy, hexyloxy, dodecyloxy and 2-ethylhexyloxy.

Besides the abovementioned hydrocarbon radicals which can stand for R and Z, the latter can also mean aryl radicals, which as well as the alkyl radicals, may be substituted. Examples are the following substituents: Phenyl, 2-, 3- or 4-methylphenyl, dimethylphenyl (mixture of isomers), p-tert.butylphenyl, 2-methoxyphenyl, 3-chlorophenyl and dichlorophenyl (mixture of isomers), 2-methoxyethyl, 2-methoxypropyl, 2-phenoxyethyl, 2-(2'-phenoxyethoxy)-ethoxy, 2-cresoxyethyl, benzyl, 4-chlorobenzyl, 2,4-dichlorobenzyl, 2-chloroethyl and substituents of formula $$CH_3(OCH_2CH_2)_p-- \qquad (VIII)$$

wherein $p$ means one of the numbers 2 to 12.

Examples for those cases, in which the radicals Z and R are connected with each other and form, together with the N-atom [formula (III)] a heterocyclic ring, are the heterocyclic substituents pyrrolidino, piperidino, hexamethylenimino and morpholino.

The invention also concerns the new compounds of formula (I) and their use as stabilizers.

For this purpose the new compounds are either incorporated in the product or material sensitive to light, oxygen and heat, or applied to its surface to form a protective film. By their stabilizing effect they protect these sensitive substances from degradation. They have a wide range of application in the processing of plastics; to name some examples, they can be employed as stabilizers for cellulose acetate, cellulose proprionate, cellulose acetobutyrate, polyethylene, polypropylene, polyvinyl chloride, polyvinyl chloride-acetate, polyamides, polystyrene, ethyl cellulose, cellulose nitrate, polyvinyl alcohol, silicon rubber, melamine-formaldehyde and urea-formaldehyde resins, allyl cast resins, polymethylmethacrylate, polyesters and polyacrylonitrile. The compounds can also be used to protect natural products such as rubber, cellulose, wool and silk from degradation. The products or material for protection may be present in the form of sheet or film, panels, tubing, rods, tapes, coatings, fibres, granules, powders or other solid forms, or as solutions, emulsions or dispersions. The stabilizers are incorporated in, or applied to these materials by the known methods. One of the main methods of application is intimate mixing of the stabilizer and the plastic material, e.g. polypropylene granules, in a kneading or other suitable machine and extrusion moulding of the mixture. This technique ensures homogeneous blending, which is important for effective protection. Extrusion moulding is employed to produce a variety of products, including films, tubing and filaments. The latter can be converted into woven fabrics.

If polypropylene, for instance, is to be processed as woven fabric the stabilizer is normally mixed with it prior to extrusion as filament yarn. However, these new stabilizers can be applied with equally good effect to textile yarns and fabrics, for example from an aqueous bath containing the compound of formula (I) in superfine dispersion. Textiles of polyester and cellulose acetate fibres are suitable for this exhaust method of application.

The plastics need not necessarily be polymerized when the new compounds are added. The latter can be blended with the monomers or prepolymers prior to the condensation or other polymerization reaction yielding the final polymer.

Besides their use for the stabilization of clear films, plastics and the like, the new stabilizers are suitable for application in or on opaque, semi-opaque and translucent materials having a surface which is subject to degradation by light, oxygen and heat. Examples of such materials are foamed plastics, opaque film and sheeting, opaque papers, transparent and opaque pigmented plastics, fluorescent pigments and automobile and furniture polishes, creams, lotions and similar products, which latter group of products may be opaque, clear or translucent. Benzene phosphonous acid esters and their stabilizing effect are known from literature. Comparing these compounds, for instance with those described in the Belgian Pat. No. 724 802, the new compounds of formula (I) have essential advantages. They are less fugitive, have less inclination for migration and are better soluble in many materials to be protected. Moreover the connection of at least two benzene nuclei in the new compounds of formula (I) has the effect, that they absorb ultra violet rays. They therefore do not only protect against heat and oxygen but also against the decomposition of sunlight. Any comparable phosphorus compounds have none such combined protective effect. In spite of this polyvalent effect it is in many cases advantageous to mix the new stabilizers with other types of light absorbers or of stabilizers.

Those mixtures of agents have often a synergistic effect and protect the treated materials at the same time in a particularly high degree against ultra violet light, heat and oxidative disintegration.

As explained above the new compounds of formula (I) can be used as stabilizers for various organic materials. Depending the kind and number of the substituents the compounds of formula (I) are more or less suited for the protection of a certain organic material. The following relations between the chemical constitution of the compounds of formula (I) and plastics, which have to be protected, have for instance been observed: To protect polypropylene, such agents are especially suited, which contain one or several aliphatic or cycloaliphatic radicals which contain at least 6, preferably 8 to 20 carbon atoms. To protect polyvinylchloride such agents are especially suited, whose substituents R contain aryl radicals, which may be substituted with lower alkyl radicals or with chloro atoms. For the protection of polyesters and of polyamides those agents are especially suited which contain several ether groups in the substituents R. The present invention concerns also the materials which contain compounds of formula (I) for stabilization. As shown above in some examples, the incorporation of the new compounds into the materials that need protection can be effected at any stage of processing according to known methods, whereby the amount of added protective agents may vary within wide limits, for instance between 0.01 and 5 %, preferably between 0.05 to 1 %, related to the materials that need protection.

In the following examples F means melting point; Kp boiling point; λwavelength, λmax the wavelength of maximum light absorption in nanometer units; parts and per cents are by weight and temperatures in degrees centigrades.

EXAMPLES FOR THE PRODUCTION OF THE INTERMEDIATE PRODUCTS OF FORMULA (IV)

a. In the absence of moisture a solution of 46.2 parts of diphenyl, 165 parts of phosphorus trichloride, and 44.8 parts of AlCl₃ is heated under reflux during the course of 3 hours; 53.5 parts of phosphorus oxychloride are subsequently added and the mixture is stirred for a further 15 minutes. After cooling to 0° the AlCl₃–POCl₃ complex, precipitated in the form of granules, is filtered off, is washed thoroughly with chlorobenzene, and the filtrate is evaporated in a vacuum. As residue 65 parts (85% of theory) of 4-diphenyl-dichlorophosphine of formula

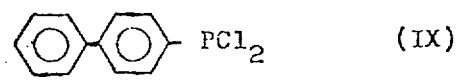

are obtained in the form of a red, light oil of a pungent smell.

b. Working up is effected as described under (a), but in place of 44.8 parts of AlCl₃, 106 parts are used, and in place of 53.5 parts of phosphorus oxychloride, 122.6 parts are used. Thus, 85.2 parts of 4,4'-diphenyl-bis-(dichlorophosphine) of formula

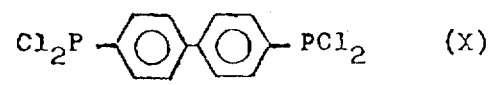

are obtained in the form of a red, light oil of a pungent smell.

c. In the absence of moisture a solution of 34.5 parts of p-terphenyl, 330 parts of phosphorus trichloride, and 52 parts of aluminium chloride are heated under reflux during the course of 5 hours; 61.3 parts of phosphorus oxychloride are subsequently added and the mixture is stirred for a further 15 minutes, is cooled to 0°, the resulting Al-complex is filtered off, is washed with phosphorus trichloride, and the filtrate is evaporated in a vacuum.

As residue 29 parts of 4,4''-(p-terphenyl)-bis-(dichlorophosphine) of formula

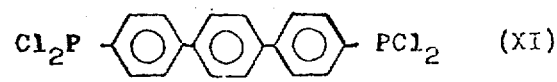

are obtained in the form of light yellow crystals.

EXAMPLES FOR THE END-PRODUCTS OF FORMULA (I)

Examples are listed in the following table 1 where the melting points of crystalline compounds are indicated in column F. These compounds melt at a temperature considerably higher than room temperature. The other indicated compounds are specified in column F as 'oil'. λmax. means the maximum of light absorption which is expressed by nanometer (nm) units. The constitution formulae indicated in table 1 are confirmed by elementary analyses.

Table 1

| Exple No. | Constitution of the compounds of general formula | | F | λmax. (nm) |
|---|---|---|---|---|

Biphenyl-P(R₁)(R₂) structure:

| Exple No. | R₁ | R₂ | F | λmax. (nm) |
|---|---|---|---|---|
| 1 | —O—C₄H₉ | R₁=R₂ | oil | 252 |
| 2 | —O—C₈H₁₇(iso) | R₁=R₂ | oil | 250 |
| 3 | —O—C₆H₄—C₉H₁₉ | R₁=R₂ | oil | 253 |
| 4 | —O—C₆H₄—C₉H₁₉ | —O—C₄H₉ | oil | 254 |
| 5 | —O—C₆H₄—C₉H₁₉ | —O—C₈H₁₇(iso) | oil | 253 |
| 6 | —S—C₁₂H₂₅ | R₁=R₂ | 42–43° | 270 |
| 7 | —S—C₆H₄—t-Bu | * R₁=R₂* | 110–111° | 255 |
| 8 | —N(CH₂CH₂)₂O (morpholino) | R₁=R₂ | 168–169° | 263 |

(R₁)(R₂)P—C₆H₄—C₆H₄—P(R₁)(R₂) structure:

| Exple No. | R₁ | R₂ | F | λmax. (nm) |
|---|---|---|---|---|
| 9 | —O—C₄H₉ | R₁=R₂ | oil | 260 |
| 10 | —O—C₈H₁₇(iso) | R₁=R₂ | oil | 259 |
| 11 | —O—C₁₃H₂₇ | R₁=R₂ | oil | 259 |
| 12 | —O—C₆H₄—t-Bu | * R₁=R₂* | 94–96° | 273 |
| 13 | —O—C₆H₄—C₉H₁₉ | R₁=R₂ | oil | 265 |
| 14 | —O—C₆H₄—C₉H₁₉ | —O—C₈H₁₇ | oil | 268 |
| 15 | —S—C₁₂H₂₅ | R₁=R₂ | 54–56° | 300 |
| 16 | —S—C₆H₄—t-Bu | * R₁=R₂* | 184–186° | 250 |
| 17 | —N(C₄H₉)₂ | R₁=R₂ | oil | 261 |

(R₂)(R₁)P—C₆H₄—C₆H₄—P(R₁)(R₂) structure:

| Exple No. | R₁ | R₂ | F | λmax. (nm) |
|---|---|---|---|---|
| 18 | —O—C₆H₄—C₉H₁₉ | —O—C₈H₁₇(iso) | oil | 271 |
| 19 | —O—C₆H₄—C₉H₁₉ | —O—C₄H₉ | oil | 262 |
| 20 | —O—C₆H₄—t-Bu | * —O—C₄H₉ | oil | 264 |
| 21 | —S—C₁₂H₂₅ | —O—C₈H₁₇(iso) | oil | 264 |

(R₁)(R₁)P—C₆H₄—C₆H₄—C₆H₄—P(R₁)(R₂) structure:

| Exple No. | R₁ | R₂ | F | λmax. (nm) |
|---|---|---|---|---|
| 22 | —O—C₈H₁₇ | R₁=R₂ | oil | 292 |
| 23 | —O—C₆H₄—t-Bu | * R₁=R₂* | 199–199.5° | 298 |
| 24 | —O—C₆H₄—C₉H₁₉ | R₁=R₂ | oil | 292 |
| 25 | —O—C₆H₄—C₉H₁₉ | —O—C₄H₉ | oil | 292 |
| 26 | —S—C₁₂H₂₅ | R₁=R₂ | 63–65° | 308 |
| 27 | —S—C₆H₄—t-Bu | * R₁=R₂* | 187–189° | 310 |
| 28 | —N(C₄H₉)₂ | R₁=R₂ | oil | 296 |

*The symbols + signify the tertiary butyl radical.

EXAMPLES FOR THE PRODUCTION OF END-PRODUCTS OF FORMULA (I)

The Examples are numbered in the same way as the corresponding compounds of the above table 1.

EXAMPLE 7

In the absence of moisture a solution of 43.5 parts of 4-diphenyldichlorophosphine [Example (a), formula (IX)] in 100 parts of toluene is added at 0°–5° to 56.8 parts of 4-tert.butyl thiophenol and 35 parts of triethylamine in 200 parts of toluene; the mixture is allowed to react over night at 40°, the precipitated triethyl ammonium chloride is filtered off, the filtrate is evaporated in a vacuum, and the oily residue is purified by crystallization from methanol-ether. Constitution formula and characterization of this compound and the compounds of the production Examples cited below are indicated in the above table 1.

EXAMPLE 9

In the absence of moisture a solution of 28.35 parts of 4,4'-diphenyl-bis-(dichlorophosphine) [Example (b), formula (X)] in 100 parts of chlorobenzene is added at 0°–5° to 23.6 parts of n-butanol and 32 parts of triethylamine in 300 parts of chlorobenzene; the mixture is allowed to react over night at 40°, the precipitated salt is filtered off, the filtrate is evaporated in a vacuum, and a light yellow oil is obtained.

EXAMPLE 13

A solution of 47.5 parts of 4,4'-diphenyl-bis-(dichlorophosphine) in 100 parts of toluene is added at 0°–5° to 117.5 parts of 4-nonylphenol and 55 parts of triethylamine in 400 parts of toluene; the mixture is allowed to react over night at 50°–60°, the precipitated triethyl ammonium chloride is filtered off, the filtrate is evaporated in a vacuum, and thus, a yellow viscous residue is obtained.

The same compound is also obtained by mixing the starting material without triethylamine and without toluene and gradual heating to 140°–160°, while there is passed carbon dioxide through the mixture, until the evolution of hydrogen chloride ceases.

EXAMPLE 15

A solution of 20.0 parts of 4,4'-diphenyl-bis-(dichlorophosphine) in 100 parts of toluene is added at 0°–5° to 45.4 parts of dodecyl mercaptan and 22.8 parts of triethylamine in 200 parts of toluene; the mixture is then allowed to react over night at 40°, the precipitated triethyl ammonium chloride is filtered off, the filtrate is evaporated in a vacuum, and the residue is crystallized from ether.

EXAMPLE 27

A solution of 31.0 parts of 4,4''-(p-terphenyl)-bis-(dichlorophosphine), Example (c), formula (XI), is added at 0°–5° to 48.1 parts of 4-tert.butyl thiophenol and 30.1 parts of triethylamine in 300 parts of toluene; the mixture is allowed to react over night at 40°, the precipitated triethyl ammonium chloride is filtered off, the filtrate is evaporated in a vacuum, and the residue is crystallized from benzene-methanol.

In place of 30.1 parts of triethylamine, 24 parts of anhydrous pyridine may also be used as acid-binding agent.

In Examples, 4, 5, 14, 18, 19, 20, 21, and 25 of table 1 there are mentioned esters of phosphonic acids which contain in the same molecule radicals derived from different alcohols, phenols or mercaptans. The production thereof is effected in analogous manner as described in the above production Examples by reacting the chlorphosphines with a mixture of the corresponding reaction partners. Thus, mixtures of esters are always obtained, aside from the main constituents which are characterized by the formulae of Examples 4, 5, 14, 18, 19, 20, 21, and 25 these mixtures also contain other esters, wherein the equivalent ratio of the radicals is shifted.

The following Examples relate to end-products which are obtained by hydrolysis of 4,4'-diphenyl-bis-(dichlorophosphine) of formula (X), partly as free phosphonous acids, partly in the form of the salts with inorganic cations.

EXAMPLE 29

80 parts of 4,4'-diphenyl-bis-(dichlorophosphine) of formula (X), produced as described in Example (b), are diluted with 20 parts of chlorobenzene and slowly added to 300 parts of water while stirring well, and the temperature is kept at 0°–5° by external cooling. The reaction is completed at 20° after 18 hours. The thin colourless precipitate is filtered off and is dried at 90° in a vacuum. The obtained crude product is appropriate for the use as stabilizer. It mainly consists of the compound of formula

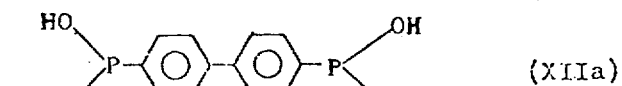

(XIIa)

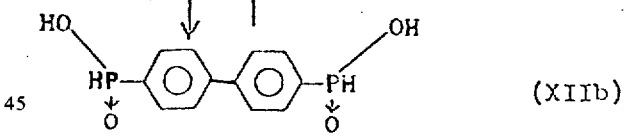

(XIIb)

and impurities which probably consist of anhydrides of the acid of formula (XII). Other impurities furthermore contain chlorine, as a small part of the chlorine atoms in the starting product of formula (X) has escaped from hydrolysis by coating with the insoluble precipitate.

EXAMPLE 30

The process described in Example 29 may be simplified by renouncing the isolation of the intermediate product of formula (X) as well as the purification thereof (precipitation of the aluminium chloride by phosphorus oxychloride).

46.2 parts of diphenyl, 106 parts of aluminium chloride, and 165 parts of phosphorus trichloride are heated under reflux during the course of 2 hours; the excess of phosphorus trichloride is subsequently removed by distillation and the viscous residue is taken up in 40 parts of chlorobenzene. Hydrolysis is then effected with 300 parts of water as described in Example 29. The obtained fine colourless powder contains 16.7 % of phosphorus, 1.1 % of chlorine, and 3.8 % of aluminium.

EXAMPLE 31

The 4-diphenyl-dichlorophosphine of formula (IX) described in Example (a) is hydrolized in accordance with methods described in Example 29; after the working up a colourless fine powder is obtained which mainly consists of the compound of the following formula

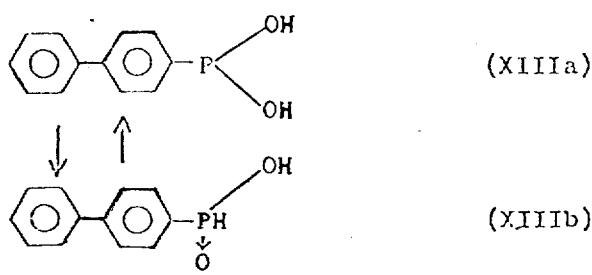

(XIIIa)

(XIIIb)

EXAMPLE 32

26 parts of the compound obtained in accordance with Example 29 are mixed by stirring with a solution of 21 parts of barium chloride in 100 parts of water and boiled under reflux during the course of 3 hours. After cooling to 5° the colourless precipitate is filtered, is washed with water and is dried at 90° in a vacuum. The resulting barium salt contains 18.9 % of barium.

In analogous manner the light green nickel salt (content of nickel is 6 %) is obtained from 25 parts of nickel acetate and the colourless zinc salt (content of zinc is 4.1 %) from 27 parts of chloride of zinc.

EXAMPLE 33

Proceeding in manner analogous to that described in Example 30 the resulting colourless powder is suspended in 400 parts of water while stirring; calcium oxide is gradually added at such an amount that after stirring at 80° for a longer period the pH value does not sink below 5°; the mixture is cooled to 5° and the precipitate is filtered. The resulting colourless salt contains 4.1 % of calcium, 6.3 % of aluminium, and 3.3 % of chlorine.

EXAMPLES FOR THE USE OF END-PRODUCTS OF FORMULA (I)

A. STABILIZATION AGAINST OXIDATIVE DEGRADATION

A few of the compounds cited in the above Examples are tested in view of their effect as stabilizers against oxygen as follows: 0.1 % of a compound of formula (I) are homogeneously incorporated in polypropylene which contains 0.2 % of 4,4'-methylen-bis-(2,6-di-tert.butylphenol) as antioxydant agent. After displacing the air, the plastics in the form of thin small plates is then kept under oxygen in a closed system. Then it is heated to 190°, whereby an overpressure of about 20 mm Hg takes place. The oxidation of the plastics results in a decrease of pressure. The rate of this decrease of pressure is small if the effectiveness of the stabilizer or the mixture of the stabilizers is high. The test results are summarized in the following table 2. The figures signify the time expressed in minutes which passes until the overpressure decreases to zero.

Table 2

| Incorporated phosphorus compounds of formula (I) Exple No. | minutes |
|---|---|
| — | 119 |
| 29 | 179 |
| 30 | 193 |
| 31 | 200 |
| 32 (Ba - salt) | 229 |
| 32 (Ni - salt) | 207 |
| 32 (Zn - salt) | 290 |
| 33 | 195 |

In a further series of tests 0.07 % of 4,4'-methylen-bis-(2,6-di-tert.butylphenol) and 0.13 % of dilaurylthiodipropionate were used for the fundamental stabilization of the polypropylene and for the rest checked comparatively as described above. The results are summarized in the following table 3.

Table 3

| Incorporated phosphorus compounds of formula (I) Exple No. | minutes |
|---|---|
| — | 48 |
| 3 | 96 |
| 5 | 61 |
| 6 | 102 |
| 9 | 78 |
| 10 | 84 |
| 12 | 105 |
| 13 | 165 |
| 14 | 81 |
| 15 | 105 |
| 18 | 102 |
| 19 | 177 |
| 20 | 98 |
| 21 | 96 |
| 26 | 89 |
| 27 | 60 |

B. STABILIZATION AGAINST BROWNISH DISCOLORATION

While incorporating 0.2 % of the stabilizer 2,2'-methylen-bis-(4-methyl-6-tert.butylphenol) in polypropylene at about 220° a brownish discoloration takes place. This discoloration may be avoided if 0.1 % of a compound of formula (I) is incorporated at the same time.

In the ageing of small plates of polypropylene in a furnace at 140° a strong brownish discoloration takes place after only 1 day if the plastics only contains 0.2 % of 2,2'-methylen-bis-(4-methyl-6-tert.butylphenol). If the plastics furthermore contains 0.1 % of a compound of the above table 1 it remains colourless after 4 days at 140°.

Formulae of representative benzene phosphonous acid compounds of the foregoing examples are as follows:

EXAMPLE 3

$$\text{Ph-C}_6\text{H}_4\text{-P}(-\text{O-C}_6\text{H}_4\text{-C}_9\text{H}_{19})_2$$

EXAMPLE 16

$$((\text{H}_3\text{C})_3\text{C-C}_6\text{H}_4\text{-S-})_2\text{P-C}_6\text{H}_4\text{-C}_6\text{H}_4\text{-P}(-\text{S-C}_6\text{H}_4\text{-C}(\text{CH}_3)_3)_2$$

EXAMPLE 19

$$\text{H}_{19}\text{C}_9\text{-C}_6\text{H}_4\text{-O} \quad \text{O-C}_6\text{H}_4\text{-C}_9\text{H}_{19}$$
$$\text{H}_9\text{C}_4\text{O}\diagdown\text{P-C}_6\text{H}_4\text{-C}_6\text{H}_4\text{-P}\diagdown\text{OC}_4\text{H}_9$$

EXAMPLE 26

$$(\text{H}_{25}\text{C}_{12}\text{-S-})_2\text{P}-\text{C}_6\text{H}_4\text{-C}_6\text{H}_4\text{-C}_6\text{H}_4-\text{P}(-\text{S-C}_{12}\text{H}_{25})_2$$

EXAMPLE 31

$$\text{C}_6\text{H}_5\text{-C}_6\text{H}_4\text{-P(OH)}_2 \rightleftarrows \text{C}_6\text{H}_5\text{-C}_6\text{H}_4\text{-PH(OH)}=\text{O}$$

What is claimed is:

1. A compound of the formula $$\begin{array}{c}\text{H-Y}\diagdown\\\text{H-Y}\diagup\text{P}\end{array}\!\!-\!\!\left(\!\!\begin{array}{c}\\\text{C}_6\text{H}_4\end{array}\!\!\right)_{\!n-1}\!\!-\!\!\text{C}_6\text{H}_4\text{-P}\diagup\!\!\begin{array}{c}\text{Y-H}\\\text{Y-H}\end{array}$$

wherein

Y is oxygen or sulphur and
$n$ is 1 or 2,
or the sodium, potassium, barium or calcium salt thereof.

2. A compound of the formula defined in claim 1 which is the barium or calcium salt thereof.

3. A compound according to claim 1 of the formula $$\begin{array}{c}\text{H-Y}\diagdown\\\text{H-Y}\diagup\text{P}\end{array}\!\!-\!\!\left(\!\!\begin{array}{c}\\\text{C}_6\text{H}_4\end{array}\!\!\right)_{\!n-1}\!\!-\!\!\text{C}_6\text{H}_4\text{-P}\diagup\!\!\begin{array}{c}\text{Y-H}\\\text{Y-H}\end{array}$$

4. A compound of claim 1, of the formula $$(\text{HO})_2\text{P}-\!\!\left(\!\!\begin{array}{c}\\\text{C}_6\text{H}_4\end{array}\!\!\right)_{\!n-1}\!\!-\!\!\text{C}_6\text{H}_4\text{-P(OH)}_2$$

wherein $n$ is 1 or 2.

5. A compound of claim 4, wherein $n$ is 1.

6. A compound of claim 5, of the formula $$(\text{HO})_2\text{P}-\text{C}_6\text{H}_4\text{-C}_6\text{H}_4-\text{P(OH)}_2$$

* * * * *